United States Patent [19]

Zoller et al.

[11] Patent Number: 5,192,795
[45] Date of Patent: Mar. 9, 1993

[54] 2-(AMINOALKYL)PYRROLEALDEHYDES, PROCESS FOR THEIR PREPARATION AND THEIR USE

[75] Inventors: Gerhard Zoller, Schöneck; Ursula Schindler, Bad Soden, both of Fed. Rep. of Germany

[73] Assignee: Cassella Aktiengellschaft, Frankfurt am Main, Fed. Rep. of Germany

[21] Appl. No.: 715,120

[22] Filed: Jun. 14, 1991

[30] Foreign Application Priority Data

Jun. 29, 1990 [DE] Fed. Rep. of Germany ....... 4020851

[51] Int. Cl.$^5$ ................. A61K 31/40; C07D 207/327; C07D 207/325
[52] U.S. Cl. .................... 548/423; 548/830; 548/536; 546/256; 546/281; 514/333; 514/343
[58] Field of Search ................. 548/536, 530; 514/423

[56] References Cited

U.S. PATENT DOCUMENTS

| | | | |
|---|---|---|---|
| 3,407,199 | 10/1968 | Pachter et al. | 548/530 X |
| 3,539,589 | 11/1970 | Teotino et al. | 548/561 |
| 3,558,652 | 1/1971 | Teotino et al. | 548/561 |
| 3,706,750 | 12/1972 | Teotino et al. | 546/208 |
| 4,785,010 | 11/1988 | Zoller et al. | 514/356 |
| 5,043,348 | 8/1991 | Zoller et al. | 548/530 X |

FOREIGN PATENT DOCUMENTS

| | | |
|---|---|---|
| 0124067 | 4/1984 | European Pat. Off. . |
| 0287988 | 10/1988 | European Pat. Off. . |
| 0434070 | 6/1991 | European Pat. Off. ............ 548/530 |
| 1720020 | 8/1972 | Fed. Rep. of Germany . |
| 6239 | 8/1968 | France . |
| 311911 | 8/1971 | U.S.S.R. ............. 548/530 |

OTHER PUBLICATIONS

Rubner et al., Photoreactive Polyimide Precursors, Siemens AG, Forschungslaboratorien D-8520 Erlanger, Postfach 3240 (date and other source materials not available).

*Primary Examiner*—Joseph Paul Brust
*Attorney, Agent, or Firm*—Perman & Green

[57] ABSTRACT

2-(Aminoalkyl)pyrrolealdehydes of the general formula I

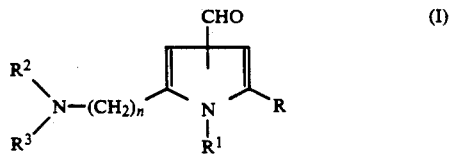

in which
R: denotes hydrogen, alkyl;
$R^1$: denotes, for example, hydrogen, alkyl, phenyl;
$R^2$ and $R^3$: denote, for example, hydrogen, alkyl or alkanoyl, have useful pharmacological properties.

16 Claims, No Drawings

2-(AMINOALKYL)PYRROLEALDEHYDES, PROCESS FOR THEIR PREPARATION AND THEIR USE

Investigations have shown that both the chemical stability and the pharmacological activities of the 2-(aminoalkyl)pyrrole derivatives described in European Patent Specification EP 0,124,067 can be clearly increased by the introduction of aldehyde groups.

The invention relates to 2-(aminoalkyl)pyrrolealdehydes of the general formula I

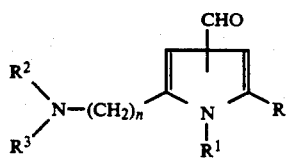 (I)

in which

R: denotes hydrogen or alkyl($C_1$–$C_3$);

$R^1$: denotes hydrogen, alkyl($C_1$–$C_5$), cyanoalkyl($C_1$–$C_4$), alkoxy($C_1$–$C_4$)carbonyl, hydroxycarbonylalkyl($C_1$–$C_4$), alkoxy($C_1$–$C_4$)carbonylalkyl($C_1$–$C_4$), $R^4(R^5)$N-carbonylalkyl($C_1$–$C_4$), alkyl($C_1$–$C_6$)carbonylaminoalkyl($C_1$–$C_4$), phenylcarbonylaminoalkyl($C_1$–$C_4$), phenoxyalkyl($C_1$–$C_3$)carbonylaminoalkyl($C_1$–$C_4$), phenyl or phenylalkyl($C_1$–$C_4$);

$R^2$ and $R^3$: independently of one another denote hydrogen, alkyl($C_1$–$C_6$), alkanoyl($C_1$–$C_6$), phenylalkyl($C_1$–$C_4$)carbonyl, phenoxyalkyl($C_1$–$C_3$) carbonyl, benzoyl or pyridylcarbonyl, or, together with the nitrogen atom to which they are bonded, form a 5-membered ring;

$R^4$ and $R^5$: independently of one another denote hydrogen, alkyl($C_1$–$C_4$) or, together with the nitrogen atom to which they are bonded, form a 5-membered ring; where the phenyl, phenoxy or benzoyl substituents can also be mono- or polysubstituted by halogen, alkyl($C_1$–$C_4$), hydroxyl, alkoxy($C_1$–$C_4$), $R^4(R^5)$N, mercapto, alkylmercapto($C_1$–$C_4$), nitro, cyano, hydroxycarbonyl, alkoxy($C_1$–$C_4$)carbonyl, alkoxy($C_1$–$C_4$)carbonylalkyl($C_1$–$C_4$), formyl or alkanoyl($C_1$–$C_4$);

n: denotes 1, 2 or 3;

and their pharmacologically acceptable acid addition salts in the case of compounds according to the invention which contain a basic group.

The invention also relates to a process for the preparation of the compounds I and their use as medicaments.

The alkyl, alkoxy, alkanoyl, alkanoyloxy, alkylene and alkoxycarbonyl radicals can be straight-chain or branched, even if they occur in combination with other radicals. Possible phenylalkyl is in particular phenethyl, preferably benzyl.

In the radicals $R^1$ and/or $R^2$ and $R^3$: phenylcarbonylaminoalkyl($C_1$–$C_4$), phenyl, phenylalkyl($C_1$–$C_4$), phenoxyalkyl($C_1$–$C_3$)carbonylaminoalkyl($C_1$–$C_4$),v phenylalkyl($c_1$–$C_4$)carbonyl, phenylalkyl($1$–$C_3$)carbonyl and benzoyl, the phenyl, phenoxy and benzoyl radicals can be monosubstituted or polysubstituted, for example monosubstituted, disubstituted or trisubstituted, preferably monosubstituted or disubstituted.

Possible halogen substituents of the phenyl, phenoxy or benzoyl radicals are fluorine, iodine, in particular bromine and preferably chlorine.

The alkyl radicals R can be methyl, ethyl, propyl and isopropyl. Methyl is preferred for the substituents R.

Examples of substituents which $R^1$ can be are: hydrogen, methyl, ethyl, propyl, pentyl, isopropyl, 1-butyl, 2-butyl, isobutyl, tert-butyl, isopentyl, cyanomethyl, 2-cyanoethyl, 3-cyanopropyl, methoxycarbonyl, n-propoxycarbonyl, i-propoxycarbonyl, n-butoxycarbonyl, t-butoxycarbonyl, benzyloxycarbonyl, methoxycarbonylmethyl, n-propoxycarbonylmethyl, i-butoxycarbonylmethyl, 2-(methoxycarbonyl)ethyl, 2-(ethoxycarbonyl)ethyl, 2-(i-propoxycarbonyl)ethyl, 2-(methoxycarbonyl)propyl, 2-(ethoxycarbonyl)propyl, aminocarbonylmethyl, 2-(aminocarbonyl)ethyl, N,N-dimethylaminocarbonylmethyl, ethylaminocarbonylethyl, pyrrolidinocarbonylmethyl, N,N-dimethylaminocarbonylethyl, phenyl, 2-methylphenyl, 3-methylphenyl, 4-methylphenyl, 2-methoxyphenyl, 3-methoxyphenyl, 4-methoxyphenyl, 3,4-dimethoxyphenyl, o-, m-, p-chlorophenyl, 4-dimethylaminophenyl, 4-mercaptophenyl, benzyl, 4-methoxybenzyl, 1-(methoxycarbonyl)-2-mercaptophenyl, 2-(acetamido)ethyl, 3-(acetamido)propyl, 2-, 3- or 4-(ethylcarbonylamino)butyl, 2-, 3- or 4-(propylcarbonylamino)butyl, methoxycarbonylmethyl, 1- or 2-methoxycarbonylethyl-, 1- or 2-ethoxycarbonylethyl, 1- or 2-propoxycarbonylethyl.

Preferred $R^1$ substituents are: hydrogen, alkyl($C_1$–$C_6$)carbonylaminoalkyl($C_1$–$C_4$), in particular 2-acetamidoethyl, alkoxy-($C_1$–$C_4$)carbonylalkyl($C_1$–$C_4$), in particular methoxycarbonylmethyl.

$R^2$ and $R^3$ can also be independently of one another, for example: hydrogen, methyl, ethyl, propyl, isopropyl, 1-butyl, 2-butyl, isobutyl, isopentyl, pentyl, formyl, acetyl, propionyl, butyryl, isobutyryl, valeryl, isovaleryl, pivaloyl, benzoyl, o-, m-, p-methylbenzoyl, 2,4-dimethylbenzoyl, o-, m-, p-methoxybenzoyl, 2,4-dimethoxybenzoyl, 3,4-dimethoxybenzoyl, o-, m-, p-chlorobenzoyl, o-, m-, p-bromobenzoyl, o-, m-, p-aminobenzoyl, o-, m-, p-hydroxybenzoyl, 4-hydroxy-3-methoxybenzoyl, 2-phenylacetyl, 2-, 3-, 4-pyridylcarbonyl, 2-, 3-or 4-nitrobenzoyl, 2-, 3- or 4-cyanobenzoyl, 2-, 3- or 4-alkoxy(C$_1$14 $_4$-C )carbonylbenzoyl, 2-, 3- or 4-ethoxycarbonylbenzoyl, 2-, 3- or 4-propoxycarbonylbenzoyl, 2-, 3- or 4-sec-butoxycarbonylbenzoyl.

Examples of 5-membered rings which $R^2$ and $R^3$, and also $R^4$ and $R^5$, together with the nitrogen atom to which they are bonded, can form, are pyrrolidin-2-on-1-yl and phthalimidyl.

Preferred substituents for $R^2$ are: alkanoyl($C_1$–$C_6$), in particular acetyl, benzoyl, phenylalkyl($C_1$–$C_4$)carbonyl, in particular benzylcarbonyl, phenoxy($C_1$–$C_4$)carbonyl, in particular phenoxymethylcarbonyl, where the phenyl group of the benzoyl or phenylalkylcarbonyl, in particular benzylcarbonyl, or the phenoxy group of the phenoxyalkyl($C_1$–$C_3$)carbonyl, in particular of the phenoxymethylcarbonyl, can preferably also carry one or two substituents, in particular halogen, nitro and/or alkoxy($C_1$–$C_4$). Possible substituents of this type are in particular chlorine, : methoxy and/or nitro. The following are preferred for $R^2$acetyl, chlorophenoxyacetyl, in particular 4-chloro-phenoxyacetyl, nitrobenzoyl, in particular 4-nitrobenzoyl and dimethoxybenzoyl, in particular 3,4-dimethoxybenzoyl.

Hydrogen is preferred for $R^3$ and 1 is preferred for n.

In many cases, the compounds according to the invention in which the aldehyde group is in the 4-position of the pyrrole nucleus show a higher pharmacological activity than if it is in the 3-position of the pyrrole nucleus.

Preferred compounds of the formula I are those wherein R, $R^1$, $R^2$, $R^3$ and n have one or in particular several meanings. The following compounds of the invention are particularly preferred: acetic acid-N-((1-(2-acetylaminoethyl)-4-formyl-5-methyl-1H-pyrrol-2-yl)methyl-amide, 1H-pyrrol-1-acetic acid-(2-(acetylaminoethyl)-4-formyl-5-methyl ester and 4-chlorophenoxy acetic acid-N-((1-(2-acetylaminoethyl-3-formyl-5-methyl-1H-pyrrol-2-yl)methyl-amide.

The 2-(aminoalkyl)pyrrolealdehydes of the general formula I according to the invention are prepared by a process in which a 2-(aminoalkyl)pyrrole of the formula II

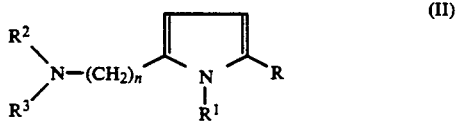

(II)

where R, $R^1$, $R^2$, $R^3$ and n have the meanings already mentioned, is formylated in a manner known per se by reaction with a formylating reagent. Many methods described in the literature are suitable for the formylation, cf., for example, Houben-Weyl, Methoden der Organischen Chemie (Methods of Organic Chemistry), 4th edition, E3, p. 16 et seq. (1983). In special cases, the variant according to Reimer-Tiemann by reaction of the pyrroles with chloroform in alkaline medium is appropriate, but the reaction of the pyrroles with 1,1-dihaloethers and Friedel-Crafts catalysts (J. Med. Chem. 15, 97 (1972)) or with trialkoxymethanes and trifluoroacetic acid (J. Org. Chem. 43 283 (1978) frequently gives better yields. The Vilsmeier synthesis, also called Vilsmeier-Haack reaction, by reaction of the pyrroles of the general formula II with a formamide and a complexing agent or Friedel-Crafts catalyst most easily leads to the compounds according to the invention (Methodicum Chinicum 5 p. 234 (1975), J. Org. Chem. 28 3052 (1963)) which, therefore is preferred for preparing the compounds of the invention.

Suitable examples of formamides are N-methylformanilide, N-N-disubstituted formamides, such as N-formylmorpholine and N-formylpiperidine, in particular however N-N-dimethylformamide. Phorsphorus oxychloride is preferred as complexing agent. Phosphorus oxychloride can be replaced by other compounds such as, for example, oxalyl chloride, thionyl chloride, sulphuryl chloride, phosgene, di- or tri-phosgene, cyanuric chloride or acid chlorides, such as acetyl chloride or benzoyl chloride. A halogen methylene dimethylammonium halogenide, also called Vilsmeier reagent, may be used instead of a formamide and a complexing agent, such as phosphorus oxychloride. The reaction is advantageously carried out in a solvent, for example an amide such as dimethylformamide, an aromatic compound, such as toluene, halogenated hydrocarbon such as 1,2-dichloroethane, methylene chloride, chlorobenzenes, an ether, such as tetrahydrofuran or ethylene glycol dimethyl ether, an ester such as ethyl acetate or butyl acetate, or nitrobenzene, or a mixture of different solvents. Isonitriles in acidic solution are also suitable as formylating agents for the preparation of the compounds according to the invention (Chem. Ber. 94, 298 (1961)). A further possibility for the formylation of the 2-(aminoalkyl)pyrrole derivatives of the formula II is reaction with s-triazine in the presence of hydrogen chloride (Arch. Pharm. 302 828). The starting compounds of the formula II needed for the preparation are known, for example, from EP-A 1-0,124,067 or U.S. Pat. No. 4,785,010 and can be prepared by the processes described therein. In the formylation of the 2-(aminoalkyl)pyrrole derivatives of the formula II, isomer mixtures are as a rule formed having the formyl group in the 3- and 4-position of the pyrrole ring, which can be separated by known separation methods, such as fractional crystallisation or column chromatography.

If the compounds of the general formula I according to the invention contain basic radicals, they form acid addition salts with inorganic or organic acids. Suitable acids are, for example: hydrogen chloride, hydrogen bromide, naphthalene-disulphonic acids, in particular naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared in the customary manner by a combination of the components, expediently in a suitable solvent or diluent.

In the synthesis of the compounds of the formula I, the acid addition salts may initially be obtained in the course of working-up. The free compounds of the general formula I can be obtained from the acid addition salts by subsequent extraction, if desired, in a known manner, for example by dissolving or suspending in water and rendering alkaline, for example with sodium hydroxide solution.

The compounds of the general formula I according to the invention and their pharmacologically acceptable acid addition salts have useful pharmacological properties. They are centrally active, for example they show encephalotropic and nootropic effects and are used for the treatment of diseases which are due to a limitation of the cerebral functions, such as cerebral insufficiency, cerebral ageing processes, reduced memory power, such as also occur in Alzheimer's disease or multi-infarct dementia. They show an excellent activity in various pharmacological tests, such as, for example, in the prolongation of survival time under sodium nitrite hypoxia according to Gibson and Blass (J. Neurochemistry 27, 37 (1976)) or in behavioral changes induced by sodium nitrite according to Peterson and Gibson (J. Pharmacol. exp. Ther. 222, 576 (1982)).

The compounds according to the invention are also highly effective in tests which are aimed directly at the detection of learning and memory power. The compounds show good effects in learning and memory tests in which amnesia or ischaemia is experimentally induced, such as, for example, in scopolamine amnesia or a cerebral ischaemia.

The compounds of the general formula I and their physiologically tolerable salts thus represent an enrichment of pharmacy.

The compounds of the general formula I according to the invention and their pharmaceutically acceptable acid addition salts can therefore be used in humans as medicaments, for example in the treatment or prevention of disorders which are due to the limitation of cerebral function and in the treatment or prevention of cerebral ageing processes.

The compounds of the general formula I and their pharmaceutically acceptable acid addition salts can be administered on their own, in mixtures with one another or in the form of pharmaceutical preparations which permit enteral or parenteral use and which contain as an active constituent an effective dose of at least one compound of the general formula I or an acid addition salt thereof, in addition to customary pharmaceutical innocuous excipients and additives. The preparations normally contain about 0.5 to 90% by weight of the therapeutically active compound.

The medicaments can be administered orally, for example in the form of pills, tablets, film tablets, coated tablets, granules, hard and soft gelatin capsules, solutions, syrups, emulsions or suspensions or aerosol mixtures. However, administration can also be carried out rectally, for example in the form of suppositories, or parenterally, for example in the form of injection solutions, or percutaneously, for example in the form of ointments or tinctures.

The pharmaceutical preparations are produced in a manner known per se in which pharmaceutically inert inorganic or organic excipients are used. For the production of pills, tablets, coated tablets and hard gelatin capsules, lactose, cornflour or derivatives thereof, talc, stearic acid or its salts etc., for example, can be used. Excipients for soft gelatin capsules and suppositories are, for example, fats, waxes, semi-solid and liquid polyols, natural or hardened oils etc. Suitable excipients for the production of solutions and syrups are, for example, water, sucrose, dextrose, glucose, polyols etc. Suitable excipients for the production of injection solutions are, for example, water, alcohols, glycerol, polyols, vegetable oils etc.

In addition to the active compounds and excipients, the pharmaceutical preparations may also contain additives, such as, for example, fillers, extenders, disintegrants, binders, lubricants, wetting agents, stabilisers, emulsifiers, preservatives, sweeteners, colorants, flavourings or aromatisers, thickeners, diluents, buffer substances, also solvents or solubilisers or agents for achieving a depot effect, and also salts for changing the osmotic pressure, coatings or antioxidants. They may also contain two or more compounds of the formula I or their pharmacologically acceptable acid addition salts and also one or more other therapeutically active substances.

Other therapeutically active substances of this type are, for example, circulation-promoting agents, such as dihydroergocristine, nicergoline, buphenine, nicotinic acid and its esters, pyridylcarbinol, bencyclane, cinnarizine, naftidrofuryl, raubasine and vincamine; positive inotropic compounds such as digoxin, acetyldigoxin, metildigoxin and lanatoglycosides; coronary dilators, such as carbocromene, dipyridamole, nifedipine and perhexiline, antianginal compounds, such as isosorbide dinitrate, isosorbide mononitrate, glycerol nitrate, molsidomin and verapamil, β-blockers, such as propranolol, oxprenolol, atenolol, metoprolol and penbutolol. The compounds can additionally be combined with other substances having nootropic activity, such as, for example, piracetam, or CNS-active substances, such as pirlindole, sulpiride etc.

The dosage can vary within wide limits and is to be suited to the individual conditions in each individual case. In general, on oral administration a daily dose of about 0.1 to 1 mg/kg, preferably 0.3 to 0.5 mg/kg of body weight is adequate to achieve effective results, on intravenous administration the daily dose is in general about 0.01 to 0.3 mg/kg, preferably 0.05 to 0.1 mg/kg of body weight. The daily dose is normally divided into several, for example 2, 3 or 4, part administrations, in particular for the administration of larger amounts. It may be necessary, depending on individual behaviour, to deviate upwards or downwards from the given daily dose. Pharmaceutical preparations normally contain 0.1 to 50 mg, preferably 0.5 to 10 mg of active compound of the formula I or of a pharmacologically acceptable salt thereof per dose.

The following Examples 1 to 7 relate to the preparation of the compounds of the formula I, the Examples A to H relate to the production of preparations of the compounds of the formula I.

EXAMPLE 1

N-((1-(2-Acetylamino ethyl)-(3)4-formyl-5-methyl-1H-pyrrol-2-yl)methyl)-4-methoxybenzamide 1.4 ml (15 mmol) of phosphorus oxychloride in 5 ml of 1,2-dichloroethane are added dropwise in the course of 10 minutes to 1.2 ml (15.5 mmol) of anhydrous dimethylformamide at 15°-20° C. The mixture is subsequently stirred for 10 minutes and 4.7 g of N-(1-(2-acetylamino)ethyl-5-methyl-1H-pyrrol-2-yl)methyl)-4-methoxybenzamide in 40 ml of 1,2-dichloroethane are then added dropwise at 15°-20° C. The mixture is stirred at room temperature for 3 h, hydrolysed using 2.7 g of sodium hydroxide, and dissolved in 50 ml of water, the solution is treated with methylene chloride and the phases are separated. The aqueous phase is extracted with methylene chloride and the combined organic phases are dried and concentrated. The residue is purified on a silica gel column using methylene chloride as the eluent.

1st compound

N-(1-(2-Acetylaminoethyl)-3-formyl-5-methyl-1H-pyrrol-2-yl)-methyl)-4methoxybenzamide Melting point: 155°-160° C.
$^1$H-NMR (DMSO, TMS), δ(ppm); 1.85 (s, 3H); 2.25 (s, 3H); 3.3 (m, 2H); 3.8 (s, 3H); 4.1 (m, 2H); 4.75 (d, 2H); 6.2 (s, 1H); 6.95 (d, 2H); 7.9 (d, 2H); 8.15 (m, 1H); 8.8 (m, 1H); 9.85 (s, 1H);

2nd compound

N-((1-(2-Acetylaminoethyl)-4-formyl-5-methyl-1H-pyrrol-2-yl)methyl)-4-methoxybenzamide Melting point: 164°-165° C.,
$^1$H-NMR (DMSO), TMS) δ(ppm); 1.85 (s, 3H); 2.5 (s, 3H); 3.3 (m, 2H); 3.8 (s, 3H); 4.0 (m, 2H); 4.5 (d, 2H); 6.3 (s, 1H); 7.0 (d, 2H); 7.9 (d, 2H); 8.2 (m, 1H); 8.75 (m, 1H); 9.75 (s, 1H);

EXAMPLE 2

N-(1-((2-Acetylaminoethyl)-(3)4-formyl-5-methyl-1H-pyrrol-2-yl)methyl)-3,4-dimethoxybenzamide 1.69 g (11 mmol) of phosphorus oxychloride are added dropwise to 0.8 g (11 mmol) of dimethylformamide in 20 ml of 1,2-dichloroethane at 10° C. The mixture is subsequently stirred for 15 minutes, 3.7 g (10 mmol) of N-((1-(2-acetylaminoethyl)-5-methyl-1H-pyrrol-2- yl)methyl)-3,4-dimethoxybenzamide in 20 ml of 1,2-dichloroethane are added dropwise and the mixture is stirred overnight at room temperature. The batch is hydrolysed at −10° C. by dropwise addition of 4.5 g (33 mmol) of potassium carbonate dissolved in 30 ml of water. The two isomers are isolated after working up analogously to Example 1.

1st compound

N-((1-(2-Acetylaminoethyl)-3-formyl-5-methyl-1H-pyrrol-2-yl)-methyl)-3,4-dimethoxybenzamide Melting point: 165°-167° C. (ethyl acetate/ether).
$^1$H-NMR (CDCl$_3$, TMS), δ(ppm); 1.9 (s, 3H); 2.3 (s, 3H); 3.6 (m, 2H); 3.9 (s, 6H); 4.2 (t, 2H); 4.75 (d, 2H); 6.3 (s, 1H); 6.75 (m, 1H); 6.86 (d, 1H); 7.4 (m, 2H); 8.35 (m, 1H); 9.75 (s, 1H);

2nd compound

N-((1-(2-Acetylaminoethyl)-4-formyl-5-methyl-1H-pyrrol-2-yl)methyl)-3,4-dimethoxybenzamide Melting point 154°-156° C. (ethyl acetate/ether).
$^1$H-NMR (CDCl$_3$, TMS), δ(ppm) 2.0 (s, 3H); 2.5 (s, 3H); 3.4 (m, 2H); 3.9 (s, 6H); 4.05 (m, 2H); 4.6 (d, 2H); 6.5 (s, 1H); 6.6 (m, 1H); 6.9 (d, 1H); 7.5 (m, 2H); 7.7 (m, 1H); 9.75 (s, 1H);

EXAMPLE 3

N-((1-(2-Acetylaminoethyl)-(3)4-formyl-5-methyl-1H-pyrrol-2-yl)methyl)-4-nitrobenzamide 2.5 g (7.26 mmol) of N-((1-(2-acetylaminoethyl)-5-methyl-1H-pyrrol-2-yl)methyl)-4-nitrobenzamide, 1.2 g (7.8 mmol) pf phosphorus oxychloride and 0.57 g (7.8 mmol) of dimethylformamide in 40 ml of methylene chloride are reacted analogously to Example 2.

1st compound

N-((1-(2-Acetylaminoethyl-3-formyl-5-methyl-1H-pyrrol-2-yl)methyl)-4-nitrobenzamide Melting point: 207°-210° (ethyl acetate/ether).
$^1$H-NMR (polysol, TMS), δ(ppm)

2nd compound

N-((1-(2-Acetylaminoethyl-4-formyl-5-methyl-1H-pyrrol-2-yl)methyl)-4-nitrobenzamide Melting point: 175°-177° C. (ethyl acetate/ether).
$^1$H-NMR (polysol, TMS), δ(ppm); 1.9 (s, 3H); 2.55 (s, 3H); 3.4 (m, 2H); 4.05 (t, 2H); 4.55 (d, 2H); 6.5 (s, 1H); 8.0 (t, 1H); 8.15 (d, 2H); 8.25 (d, 2H); 9.1 (t, 1H); 9.8 (s, 1H);

EXAMPLE 4

N-((1-(2-Acetylaminoethyl)-4-formyl-5-methyl-1H-pyrrol-2-yl)methyl)acetamide 4.9 g of N-((1-(2-acetylaminoethyl)-5-methyl-1H-pyrrol-2-yl)methyl)acetamide in 70 ml of 1,2-dichloroethane are added dropwise to 3.0 g (21 mmol) of chloromethylenedimethylammonium chloride in 30 ml of 1,2-dichloroethane at 10° C. The mixture is subsequently stirred for 90 min, hydrolysed using potassium carbonate solution and worked up as described in Example 1.

Melting point: 162°-164° C. (isopropanol/ligroin).
$^1$H-NMR (CDCl$_3$, TMS), δ(ppm); 1.9 (s, 3H)); 1.85 (s, 3H), 2.5 (s, 3H); 3.25 (m, 2H); 3.9 (t, 2H); 4.2 (d, 2H); 6.3 (s, 1H); 8.1 (t, 1H); 8.2 (t, 1H); 9.7 (s, 1H);

EXAMPLE 5

((2-Acetylaminomethyl)-(3)4-formyl-5-methyl)methyl 1H-pyrrole-1-acetate 6.2 g (27 mmol) of ((2-acetylaminomethyl)-5-methyl)-methyl 1H-pyrrole-1-acetate and 3.9 g (30 mmol) of chloromethylenedimethylammonium chloride in 100 ml of 1,2-dichloroethane are reacted analogously to Example 4.

1st compound ((2- Acetylaminomethyl)-3-formyl-5-methyl) methyl 1H-pyrrole-1-acetate Melting point: 145°-147° C. (ethyl acetate).
$^1$H-NMR (CDCl$_3$, TMS) δ(ppm); 1.95 (s, 3H); 2.2 (s, 3H), 3.8 (s, 3H); 4.5 (s, 2H); 4.95 (s, 2H); 6.35 (s, 1H); 7.0 (m, 1H); 9.75 (s, 1H);

2nd compound ((2- Acetylaminomethyl)-4-formyl-5-methyl)methyl 1H-pyrrole-1-acetate Melting point: 135°-137° C. (ethyl acetate/ether).
$^1$H-NMR: (CDCl$_3$, TMS) δ(ppm); 2.0 (s, 3H); 2.4 (s, 3H); 3.8 (s, 3H); 4.35 (s, 2H); 4.75 (s, 2H); 6.45 (s, 1H); 6.5 (m, 1H); 9.75 (s, 1H);

EXAMPLE 6

N-((1-(2-Acetylaminoethyl)-(3)-4-formyl-5-methyl-1H-pyrrol-2-yl)methyl)-4-chlorophenoxyacetamide 4.9 g (49 mmol) of phosgene are introduced in the course of 30 minutes into a mixture of 3.9 ml (50 mmol) of dimethylformamide and 70 ml of methylene chloride at 0° C. with cooling and exclusion of moisture and with nitrogen blanketing. The mixture is subsequently stirred at 0° C. for 45 minutes and 13.6 g (37 mmol) of N-((1-(2-acetylaminoethyl)-5-methyl-1H-pyrrol-2-yl)methyl)-4-chlorophenoxyacetamide in 30 ml of methylene chloride are added dropwise in the course of 30 minutes. The mixture is stirred at 0° C. for 20 minutes and at 10°-15° C. for 1 h, hydrolysed with potassium carbonate solution after reaction is complete and worked up as described in Example 2.

1st compound

N-((1-(2-Acetylaminoethyl)-3-formyl-5-methyl-1H-pyrrol-2-yl)methyl)-4-chlorophenoxyacetamide Melting point: 177°-179° C.
$^1$H-NMR (DMSO, TMS), δ(ppm); 1.8 (s, 3H); 2.2 (s, 3H); 3.25 (m, 2H); 3.95 (t, 2H); 4.5 (s, 2H); 4.6 (d, 2H); 6.2 (s, 1H); 6.95 (dd, 2H); 7.3 (dd, 2H); 8.1 (t, 1H), 8.7 (t, 1H); 9.85 (s, 1H);

2nd compound

N-((1-(2-Acetylaminoethyl)-4-formyl-5-methyl-1H-pyrrol-2-yl)methyl)-4-chlorophenoxyacetamide Melting point: 150°-152° C.
$^1$H-NMR (DMSO, TMS); δ(ppm); 1.8 (s, 3H); 2.5 (s, 3H); 3.25 (m, 2H); 3.95 (t, 2H); 4.3 (d, 2H); 4.55 (s, 2H); 6.3 (s, 1H); 7.0 (dd, 2H); 7.35 (dd, 2H); 8.1 (t, 1H); 8.55 (t, 1H); 9.75 (s, 1H);

EXAMPLE 7

N-(((3)4-Formyl-5-methyl-1H-pyrrol-2-yl)methyl)-4-chlorophenoxyacetamide 11 g (39 mmol) of N-((5-methyl-1H-pyrrol-2-yl)methyl)-4-chlorophenoxyacetamide and 5.7 g (45 mmol) of chloromethylenedimethylammonium chloride are reacted in 380 ml of 1,2-dichloroethane analogously to Example 4.

1st compound

N-((3-Formyl-5-methyl-H-pyrrol-2-yl)methyl)-4-chlorophenoxyacetamide

Melting point: 171°–174° C.
$^1$H-NMR (CDCl$_3$, TMS), δ(ppm); 2.3 (s, 3H)) ; 4.35 (d, 2H); 4.5 (s, 2H); 6.3 (s, 1H); 6.85 (d, 2H); 6.9 (m, 1H); 7.25 (d, 2H); 9.3 (s, 1H); 11.1 (s, 1H);

2nd compound

N-((4-Formyl-5-methyl-1H-pyrrol-2-yl)methyl)-4-chlorophenoxyacetamide

Melting point: 181°–183° C. (ethyl acetate).
$^1$H-NMR (DMSO, TMS), δ(ppm); 2.4 (s, 3H); 4.25 (d, 2H); 4.5 (s, 2H); 6.15 (s, 1H); 6.95 (dd, 2H); 7.3 (dd, 2H)) ; 8.4 (s, 1H); 9.75 (s, 1H); 11.2 (s, 1H);

EXAMPLE 8

Acetic acid-N-(((3)4-formyl-5-methyl-1H-pyrrol-2-yl)methyl-)amide 5.3 g (35 mmol) of acetic acid-N-((5-methyl-1H-pyrrol-2-yl)methyl)-amide and 5.0 g (39 mmol) of chloromethylenedimethylammoniumchloride are reacted in 120 ml of 1,2-dichlorethane in analogy with Example 4.

1st Compound

Acetic acid-N-((3-formyl-5-methyl-1H-pyrrol-2-yl)methyl)-amide

Melting point: 147°–150° C.
$^1$H-NMR (CDCl$_3$, TMS), δ(ppm); 1.85 (s, 3H); 2.15 (s, 3H); 4.45 (d, 2H); 6.05 (s, 1H); 8.2 (b, 1H); 9.75 (s, 1H); 11.2 (s, 1H);

2nd Compound

Acetic acid-N-((4-formyl-5-methyl-1H-pyrrol-2-yl)methyl)-amide

Melting point: 178°–180° C. 1H-NMR (CDCl$_3$, TMS), δ(ppm); 1.85 (s, 3H); 2.4 (s, 3H); 4.15 (d, 2H); 6.2 (s, 1H); 8.15 (b, 1H); 9.7 (s, 1H); 11.25 (s, 1H).

Example A to H below describe pharmaceutical preparations

Example A
Emulsions containing 3 mg of active compound per 5 ml can be prepared according to the following recipe:

| | |
|---|---|
| Active compound | 0.06 g |
| Neutral oil | q.s. |
| Sodium carboxymethylcellulose | 0.6 g |
| Polyoxyethylene stearate | q.s. |
| Pure glycerol | 0.6–2 g |
| Flavourings | q.s. |
| Water (demineralised distilled) | ad 100 ml |

Example B
Tablets can be prepared according to the following formulation:

| | |
|---|---|
| Active compound | 2 mg |
| Lactose | 60 mg |
| Cornflour | 30 mg |
| Soluble starch | 4 mg |
| Magnesium stearate | 4 mg |
| | 100 mg |

Example C
The following composition is suitable for the production of soft gelatin capsules containing 5 mg of active compound per capsule:

| | |
|---|---|
| Active compound | 5 mg |
| Mixture of triglycerides from coconut oil | 150 mg |
| Capsule contents | 155 mg |

Example D
The following formulation is suitable for the production of coated tablets:

| | |
|---|---|
| Active compound | 3 mg |
| Cornflour | 100 mg |
| Lactose | 55 mg |
| sec. calcium phosphate | 30 mg |
| Soluble starch | 3 mg |
| Magnesium stearate | 5 mg |
| Colloidal silicic acid | 4 mg |
| | 200 mg |

Example E
Coated tablets, containing an active compound according to the invention and another therapeutically active substance:

| | |
|---|---|
| Active compound | 6 mg |
| Propranolol | 40 mg |
| Lactose | 90 mg |
| Cornflour | 90 mg |
| sec. calcium phosphate | 34 mg |
| Soluble starch | 3 mg |
| Magnesium stearate | 3 mg |
| Colloidal silicic acid | 4 mg |
| | 270 mg |

Example F
Coated tablets, containing an active compound according to the invention and another therapeutically active substance:

| | |
|---|---|
| Active compound | 5 mg |
| Pirlindol | 5 mg |
| Lactose | 60 mg |
| Cornflour | 90 mg |
| sec. calcium phosphate | 30 mg |
| Soluble starch | 3 mg |
| Magnesium stearate | 3 mg |
| Colloidal silicic acid | 4 mg |
| | 200 mg |

Example G
Capsules, containing an active compound according to the invention and another therapeutically active substance:

| | |
|---|---|
| Active compound | 5 mg |
| Nicergoline | 5 mg |
| Cornflour | 185 mg |
| | 195 mg |

Example H
Injection solutions containing 1 mg of active compound per ml can be prepared by the following recipe:

| | |
|---|---|
| Active compound | 1.0 mg |
| Polyethylene glycol 400 | 0.3 mg |
| Sodium chloride | 2.7 mg |
| Water for injection purposes to | 1.0 ml |

For the purpose of pharmacological testing the compounds of the invention are examined, for example, in accordance with the two following methods:

I. Nitrite Hypoxia in Mice

In this test, cerebral hypoxia leading to massive disturbances in the behaviour of the animals is generated in mice with NaNO$_2$ (175 mg/kg subcutaneously) in accordance with the method of Gibson and Blass (J. Neurochem. 27, 37 (1976). It is ascertained whether the ability to hold onto a rotating rod is influenced by premedication with the test substance. The results are shown in the following Table 1:

TABLE 1

Percentage reversal of disturbance in the ability to hold after administration of 175 mg/kg of NaNO$_2$ subcutaneously and premedication with the compounds of the general formula I

| Compound of general formula I acc. to Example | Dose (mg/kg) (p.o.) | Percentage reversal of hypoxia effect |
|---|---|---|
| 1a | 3 | 36 |
| 1b | 3 | 63 |
| 2a | 3 | 71 |
| 2b | 3 | 68 |
| 3a | 3 | 58 |
| 3b | 3 | 55 |
| 4 | 0.03 | 77 |
| 5b | 0.3 | 34 |
| 6a | 0.03 | 69 |
| Piracetam (known comparison substance) | 10 | 19 |

In the above Examples the letter "a" each means the first compound and "b" each means the second compound of the respective Example.

II. Passive Avoidance Test

The test apparatus is a light-dark box with a grid floor which can be electrified in the dark part.

55 minutes after administration of a control and preparation injection, inexperienced male mice are treated with scopolamine hydrobromide (3 mg/kg intraperitoneally). 5 minutes later, the mice are placed in the light section of the box. After changing over to the dark section of the box, they are given an unpleasant electric shock to the feet. After 24 hours, each mouse is again placed in the light section of the test apparatus and the residence time (maximum 180 seconds) is measured. The animals treated with an active dose of a preparation and scopolamine show a long residence time, as do the animals which have not been treated with scopolamine, whereas those treated with a control injection and scopolamine show a short residence time. The results are shown in the following Table 2.

TABLE 2

Percentage attenuation of the scopolamine-induced amnesia, detectable by an increase in the time taken to step into the dark part of the passive avoidance test chamber.

| Compound of general formula I acc. to Example | Dose (mg/kg) (p.o.) | Percentage attenuation |
|---|---|---|
| 1a | 10 | 34 |
| 1b | 10 | 29 |
| 2b | 3 | 33 |
| 3b | 3 | 25 |
| 4 | 0.3 | 79 |
| 6a | 0.3 | 41 |
| Piracetam (known comparison substance) | 30 | 18 |

In the above Examples the letter "a" each means the first compound and "b" each means the second compound of the respective Example.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

We claim:

1. 2(Aminoalkyl)pyrrolealdehyde of the formula I

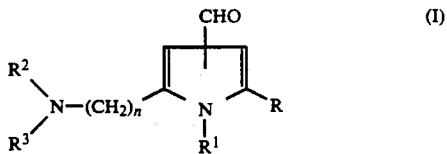

in which
R: denotes hydrogen or alkyl (C$_1$–C$_3$);
R$^1$: denotes hydrogen, cyanoalkyl (C$_1$–C$_4$), hydroxycarbonylalkyl (C$_1$–C$_4$), alkoxy(C$_1$–C$_4$)carbonylalkyl(C$_1$–C$_4$), R$^4$(R$^5$)N-carbonylalkyl-C$_1$–C$_4$, alkyl(C$_1$–C$_6$)carbonylaminoalkyl(C$_1$–C$_4$), phenylcarbonylaminoalkyl (C$_1$–C$_4$), phenoxyalkyl (C$_1$–C$_3$)-carbonyl-aminoalkyl(C$_1$–C$_4$);
R$^2$ and R$^3$: independently of one another denote hydrogen, alkyl(C$_1$–C$_6$), alkanoyl(C$_1$–C$_6$), phenylalkyl(C$_1$–C$_4$)carbonyl, phenoxyalkyl (C$_1$–C$_3$)carbonyl, benzoyl or pyridylcarbonyl;
R$^4$ and R$^5$ independently of one another denote hydrogen, or alkyl(C$_1$–C$_4$); where the phenyl, phenoxy or benzoyl substituents can also be mono- or disubstituted by halogen, alkyl(C$_1$–C$_4$), hydroxyl, alkoxy(C$_1$–C$_4$), R$^4$(R$^5$)N, mercapto, alkylmercapto(C$_1$–C$_4$), nitro, cyano, hydroxycarbonyl, alkoxy(C$_1$–C$_4$) carbonyl, alkoxy(C$_1$–C$_4$)carbonylalkyl(C$_1$–C$_4$), formyl or alkanoyl-(C$_1$–C$_4$);
n: denotes 1, 2 or 3;
and pharmacologically acceptable acid addition salts thereof in the case of compounds which contain a basic group.

2. 2-(Aminoalkyl)pyrrolealdehyde according to claim 1, characterised in that R denotes methyl.

3. 2-(Aminoalkyl)pyrrolealdehyde according to claim 1 characterised in that R$^1$ denotes hydrogen, alkyl(-C$_1$–C$_6$)carbonylaminoalkyl(C$_1$–C$_4$) or alkoxy(C$_1$–C$_4$-)carbonylalkyl(C$_1$–C$_4$).

4. 2-(Aminoalkyl)pyrrolealdehyde according to claim 3 characterised in that R$^1$ denotes 2-acetamidoethyl.

5. 2-(Aminoalkyl)pyrrolealdehyde according to claim 3 characterised in that R$^1$ denotes methoxycarbonylmethyl.

6. 2-(Aminoalkyl)pyrrolealdehyde according to claim 1 characterised in that R$^2$ denotes alkanoyl(C$_1$–C$_6$), benzoyl, phenylalkyl(C$_1$–C$_4$)carbonyl or phenoxyalkyl(C$_1$–C$_3$)carbonyl, where the phenyl group of the benzoyl or phenylalkylcarbonyl or the phenoxy group of the phenoxyalkyl(C$_1$–C$_3$)carbonyl carries from zero to two substituents from the group halogen, nitro and alkoxy(C$_1$–C$_4$).

7. 2-(Aminoalkyl)pyrrolealdehyde according to claim 6, characterised in that R$^2$ denotes acetyl, benzoyl, benzylcarbonyl or phenoxymethylcarbonyl, where the phenyl group of the benzoyl or benzylcarbonyl, or the phenoxy group of the phenoxymethylcarbonyl carries from zero to two substituents from the group halogen, nitro and alkoxy(C$_1$–C$_4$).

8. N-((1-(2-Acetylaminoethyl)-4-formyl-5-methyl-1H-pyrrol-2-yl)methyl)acetamide.

9. 1H-pyrrol-1-acetic acid-((2- acetylaminomethyl)-4-formyl-5-methyl)-methyl ester.

10. 4-Chlorophenoxy acetic acid-N-((1-(2-acetylaminoethyl-3-formyl-5-methyl-1H-pyrrol-2-yl)methyl)-amide.

11. Process which comprises administering an effective amount of a 2-(aminoalkyl)pyrrolealdehyde or of a pharmacologically acceptable acid addition salt thereof, of claim 1 to a host in need thereof for the treatment of diseases in the human which are due to a limitation of cerebral function.

12. Pharmaceutical preparation for the effective treatment of diseases in the human which are due to a limitation of cerebral function, characterized in that it contains, as an active compound, an effective amount of one or more 2-(aminoalkyl)-pyroolealdehydes of formula I as defined in claim 1 or one or more of their pharmacologically acceptable acid addition salts together with one or more pharmaceutically acceptable excipients.

13. 2-(Aminoalkyl)pyrrolealdehyde according to claim 1 in which

R: denotes methyl;

$R^1$: denotes hydrogen, alkoxy($C_1$–$C_4$)carbonylalkyl($C_1$–$C_4$), or alkyl ($C_1$–$C_6$)carbonylaminoalkyl($C_1$–$C_4$);

$R^2$: denotes alkanoyl($C_1$–$C_6$), benzoyl, phenylalkyl($C_1$–$C_4$)-carbonyl or phenoxyalkyl($C_1$–$C_3$)carbonyl, where the phenyl group of the benzoyl or phenylalkylcarbonyl or the phenoxy group of the phenoxyalkyl($C_1$–$C_3$)carbonyl carries from zero to two substituents from the group halogen, nitro and alkoxy($C_1$–$C_4$);

$R^3$: denotes hydrogen;

n: denotes 1.

14. 2-(Aminoalkyl)pyrrolealdehyde according to claim 13, characterized in that $R^1$ denotes 2-acetamidoethyl.

15. 2-(Aminoalkyl)pyrrolealdehyde according to claim 13, characterized in that $R^1$ denotes methoxycarbonylmethyl.

16. 2-(Aminoalkyl)pyrrolealdehyde according to claim 13, characterized in that $R^2$ denotes acetyl, benzoyl, benzyl-carbonyl or phenoxymethylcarbonyl, where the phenyl group of the phenoxymethylcarbonyl carries from zero to two substituents from the group halogen, nitro and alkoxy($C_1$–$C_4$).

* * * * *